United States Patent [19]

Johnson

[11] Patent Number: 4,894,011
[45] Date of Patent: Jan. 16, 1990

[54] APPLIANCE FOR USE IN APPLYING FILLER MATERIAL TO AN ENDODONTICALLY PREPARED ROOT CANAL

[76] Inventor: William B. Johnson, 4254 E. 78th St., Tulsa, Okla. 74136

[21] Appl. No.: 265,942

[22] Filed: Nov. 2, 1988

[51] Int. Cl.[4] .............................................. A61C 5/02
[52] U.S. Cl. ..................................................... 433/81
[58] Field of Search ........................................... 433/81

[56] References Cited

U.S. PATENT DOCUMENTS

| 1,969,808 | 6/1934 | Lentulo | 433/224 |
| 3,861,043 | 1/1975 | Lieb et al. | 433/225 |
| 4,353,698 | 10/1982 | McSpadden | 433/81 |
| 4,397,634 | 10/1982 | Biggs | 433/225 |
| 4,457,710 | 7/1984 | McSpadden | 433/81 |
| 4,758,156 | 7/1988 | Johnson | 433/81 |

OTHER PUBLICATIONS

Journal of Endodontics, "A New Gutta-Percha Technique", vol. 4, No. 6, Jun. 1978, pp. 184–188.

Primary Examiner—Robert Peshock
Attorney, Agent, or Firm—Head & Johnson

[57] ABSTRACT

An improved appliance for use in applying filler material, such as gutta-percha or the like, to an endodontically prepared root canal of a tooth in the form of an elongated shaft of material having high biological tolerance, the shaft having a handle portion at the proximal end portion, the shaft distal end portion having a surface configuration adaptable to retain filler material formed thereon and being positionable in a root canal, the shaft distal and proximal portion being severable from each other whereby the distal portion and filler material therein remain in the root canal. In the preferred arrangement the shaft distal portion surface is defined by a spiral groove.

16 Claims, 3 Drawing Sheets

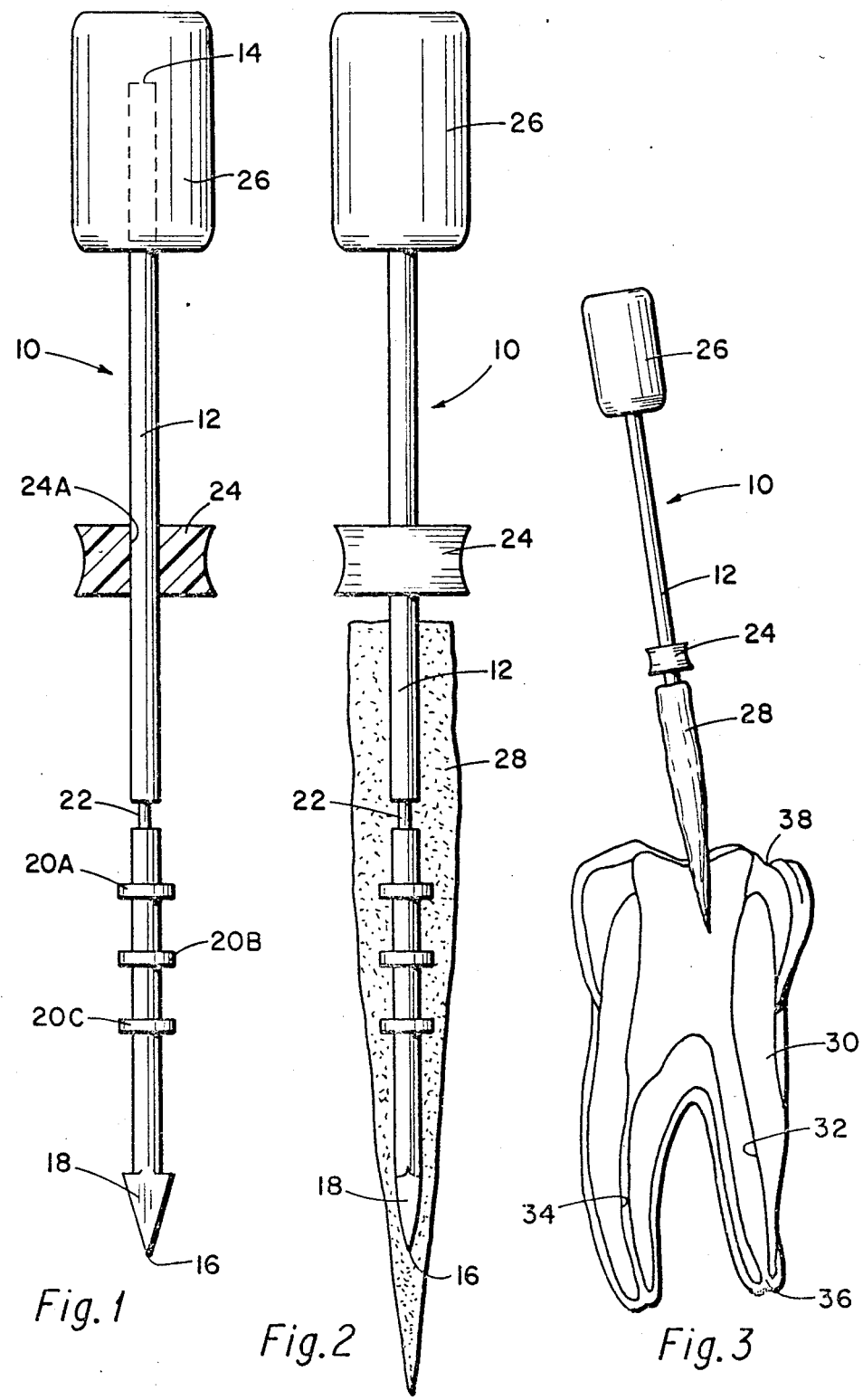

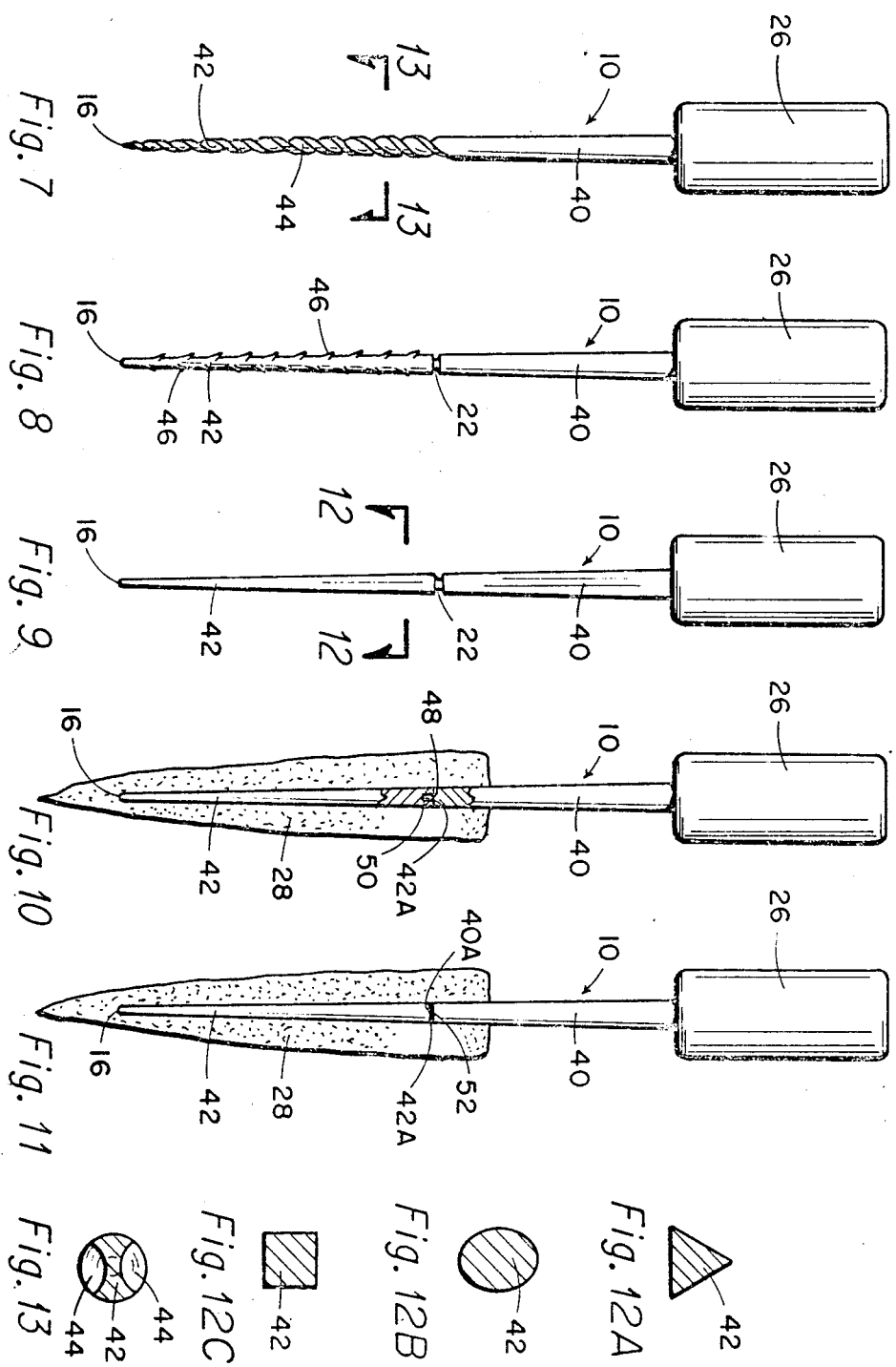

APPLIANCE FOR USE IN APPLYING FILLER MATERIAL TO AN ENDODONTICALLY PREPARED ROOT CANAL

SUMMARY OF THE INVENTION

This disclosure is related to the subject matter of U.S. Pat. No. 4,758,156, issued July 19, 1988, to William B. Johnson, entitled: "A TOOL FOR USE IN APPLYING FILLING MATERIAL TO AN ENDODONTICALLY PREPARED ROOT CANAL", which application is incorporated herein by reference.

The conventional techniques for performing endodontic therapy on teeth are time consuming and often do not adequately ensure that the entire canal system is filled with the repair material. Experience has shown that it is not possible to remove all pulpal remnants and contaminants from a root canal with current preparation techniques. If the said pulpal remnants and contaminants are thoroughly entombed in the repair material, the endodontic therapy will be successful. If said remnants and contaminants are not thoroughly entombed, there is a high probability of failure of the endodontic therapy. Complete entombment of the remnants and contaminants requires complete obduration of the canal system. Experience has shown failure to completely obdurate the canal system to be the primary cause of failure in endodontic therapy.

The appliance of the present disclosure is in the form of a rigid carrier member having a proximal portion and a distal portion with the distal portion coated with gutta-percha or similar filler material. The carrier member is a tapered, slender rod. The carrier member may be constructed of any material which is of sufficient rigidity and non-toxic when left in the root canal. One material that has been employed successfully is stainless steel. A highly biocompatible plastic or metal carrier member also works successfully.

In the present disclosure the appliance has characteristically a proximal end portion and a distal end portion with the distal end portion being positionable into the full length of a root canal and a handle portion extending above the tooth crown. The distal and proximal portions of the appliance are constructed so that after the distal portion is fully seated in the root canal the portions can be separated from each other.

In one embodiment the appliance has a telescopic fit between the distal and the proximal portion. In another embodiment the appliance has the distal and proximal portions secured to each other by bonding cement. In a still different embodiment, the distal and proximal portions are separated by an area of reduced crosssectional dimensions so that it can be broken off by moving the proximal portion back and forth relative to the distal portion to break the tool in the area of weakness.

In another embodiment the distal and proximal portions do not have a defined point of severance and the dentist severs the tool after the distal portion has been fully seated in a root canal.

A further improvement of the appliance of this invention is the provision wherein the cross-sectional configuration of the appliance in at least the distal portion is non-circular, such as triangular, square, oval or the like. In still a different preferred embodiment the distal portion has a spiral groove therein to assist in retention of the filler material on the surface thereof and in compaction of the filler material within the root canal. Another embodiment includes the use of a surface formed by integral projections which serve to retain the filler material on the distal portion.

A disc-shaped washer is incorporated on the shaft of the carrier member and serves to act as a stopping plug at the coronal opening of the canal and thus to prevent viscous flow of the gutta-percha out of the said canal during the insertion process. The disc-shaped washer is also used for distance measurement.

The filler material is molded to the carrier member in a tapered or conically-shaped manner so as to facilitate the introduction into the typical canal taper with sufficient material to ensure complete filling of the said canal and thereby complete obduration of the canal.

The devices may be manufactured in a variety of sizes to correspond to standard endodontic files.

In using the appliance of this invention the root canal is first prepared in the standard manner by broaching with endodontic files. An appliance of proper size is prepared with filler material which then may be heated over a flame so that the filler material becomes thermoplasticized. The heated appliance is then inserted into the root canal with firm apical force. The proximal of the appliance is then separated from the distal portion to leave the distal portion with the filler material thereon in the root canal.

The proximal portion is then removed while holding the stopping plug or washer against the tooth and the remainder of the endodontic therapy is completed using conventional procedures.

In another arrangement of the appliance, the shaft may be without a defined means of severing the proximal portion from the distal portion. In this arrangement the distal portion with filler material thereon is inserted in the root canal to the full depth. The dentist then using a rotating burr or cutter pliers severs the proximal portion from the distal portion; or the dentist may form a point of weakness by forming a notch in the shaft with a rotating burr or cutting pliers and then finish separating the distal portion from the proximal portion by bending the shaft back and forth at the point of weakness. In this manner, the appliance can be used in any depth of root canal without consideration of matching the length of the distal portion to the depth of the root canal.

One of the advantages of leaving the distal portion of the carrier in the tooth, according to the principals of this invention, is that it greatly reduces the volume of filler material employed and therefor the effect of shrinkage of the filler material.

For more information as to background material relating to the present invention, reference may be had to pages 184 through 188 of the *Journal of Endodontics*, Volume 4, No. 6, June 1978 which describes a new guttapercha technique in which the gutta-percha is formed around an endodontic file.

A better understanding of the invention will be had by reference to the following description and claims, taken in conjunction with the attached drawings.

DESCRIPTION OF THE DRAWINGS

FIG. 1 is an enlarged elevational view of the appliance or carrier member of the present invention. The appliance includes a slidable stopper or washer which is shown in cross-section.

FIG. 2 is an elevational view as in FIG. 1 showing the lower portion of the appliance as encapsulated in a conically-shaped quantity of filler material such as gutta-percha. As shown in FIG. 2, the apparatus is ready for use in filling an endodontically prepared root canal.

FIG. 3 shows a tooth in cross-section with the root canal having been endodontically prepared and showing the appliance of this invention, in reduced scale, as being employed to apply filler material to one of the endodontically prepared roots.

FIG. 7 is an elevational view of an alternate embodiment of the invention in which the appliance distal portion is formed with the spiral groove for improved retention of the filler material. In this embodiment there is no preselected point of severance or separation of the appliance distal portion from the proximal portion. Instead, the dentist after fully inserting the distal portion in a root canal severs the proximal portion using a rotating burr or cutter pliers; or at least forms a point of weakness so the proximal portion can be broken off by moving it back and forth.

FIG. 8 is an elevational view of the appliance as in FIG. 7 in which the distal portion is provided with integral projections which serve to augment retention of the filler material.

FIG. 9 is an embodiment of the appliance as in FIGS. 7 and 8 in which the distal portion has a noncircular cross-sectional configuration.

FIG. 10 is an elevational view of the appliance showing the arrangement wherein the distal portion is severable from the proximal portion by a telescopic inner connection between the two portions and showing filler material secured on the distal portion.

FIG. 11 is an elevational view as in FIG. 10 and showing the arrangement wherein the distal portion is secured to the proximal portion by means of a bonding cement.

FIG. 12A is a cross-sectional view of FIG. 9 showing the arrangement wherein the non-circular configuration of the distal portion is triangular.

FIG. 12B is a cross-sectional view of FIG. 9 in which the distal portion is oval.

FIG. 12C is a cross-sectional view of FIG. 9 in which the distal portion is square.

FIG. 13 is a cross-sectional view of the distal portion of the appliance of FIG. 7 to show the spiral groove in the external surface.

DETAILED DESCRIPTION OF THE PREFERRED EMBODIMENTS

Figure 4:
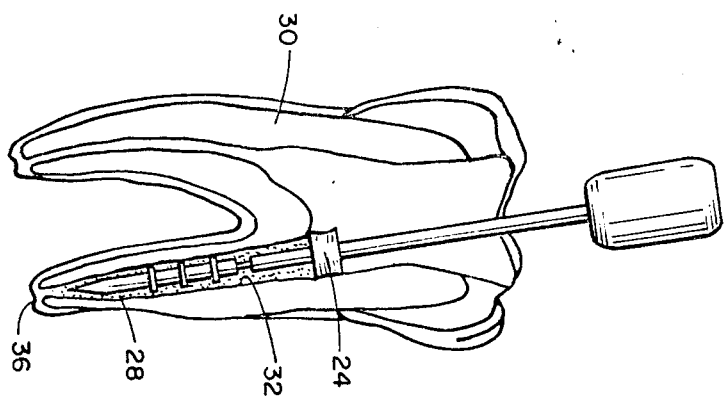
FIG. 4 is a cross-sectional view of the tooth as in FIG. 3 showing the appliance inserted into the root canal.

Referring to the drawings and first to FIG. 1, the appliance which is a carrier member is generally indicated by numeral 10 and is formed of an elongated shaft 12 having a proximal end 14 and distal end 16. While the shaft may be of a variety of cross-sectional configurations, the preferred and simplest shape is that of a circular cross-sectioal configuration so that when the shaft is positioned in a root canal of a tooth, as will be hereinafter more specifically described, the flared end portion 18 resists rotation of the shaft. Integrally formed on the shaft are a plurality (three being shown) of spaced apart enlarged cross-sectional dimensioned portions 20A through 20C. When the shaft is circularly cross-sectional as preferred, the enlarged diameter portion 20A, 20B and 20C are also preferably an enlarged circular cross-sectional configuration.

Positioned between the enlarged diameter portion 20A, and the proximal end 14 is a reduced torque resistance area 22. This is in the form, as shown, of a groove formed around the shaft. Between groove 22 and the proximal end 14 is a sliding stopper or washer 24 having an opening 24A therein which slidably receives shaft 12.

Affixed to the shaft at the proximal end 14 is a handle portion 26. Handle 26 is of a diameter larger than that of a shaft 12 and may be integral with the shaft or secured to the shaft and made of a material such as plastic.

FIG. 2 shows the appliance ready for use in inserting a filler material into the root canal of an endodontically prepared tooth. FIG. 2 shows, in cross-section, filler material 28 formed on the appliance 10. The filler materiala 28 may be such as gutta-percha which can be formed by hand onto appliance 10. After forming, the gutta-percha may be warmed in a flame to the proper stage.

FIG. 3 shows a tooth 30 having root canal 32 and 34 therein. A canal 32 has been endodontically prepared in the standard technique such as by the use of files to remove the root pulp and to prepare, as well as possible, a clean canal. Appliance 10, with the filler material 28 molded thereon, is ready for use for filling the root canal 32. The apex of the root canal is indicated at 36 with the tooth crown or coronal portion being indicated by numeral 38.

Figure 5:
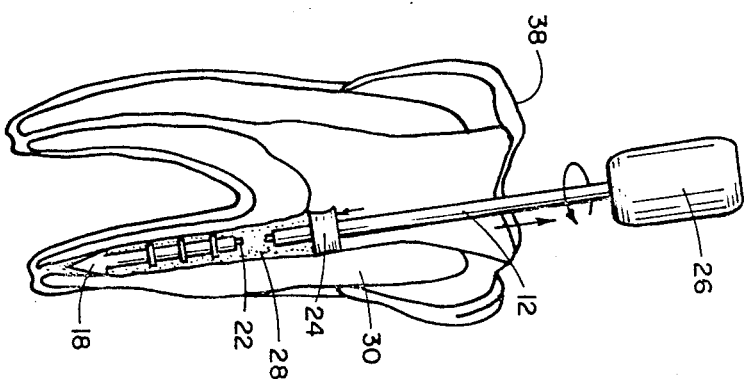
FIG. 5 shows the next step in a sequence of applying filler material to the root canal wherein the tool has been rotated to sever the proximal portion from the distal portion.
Figure 6:
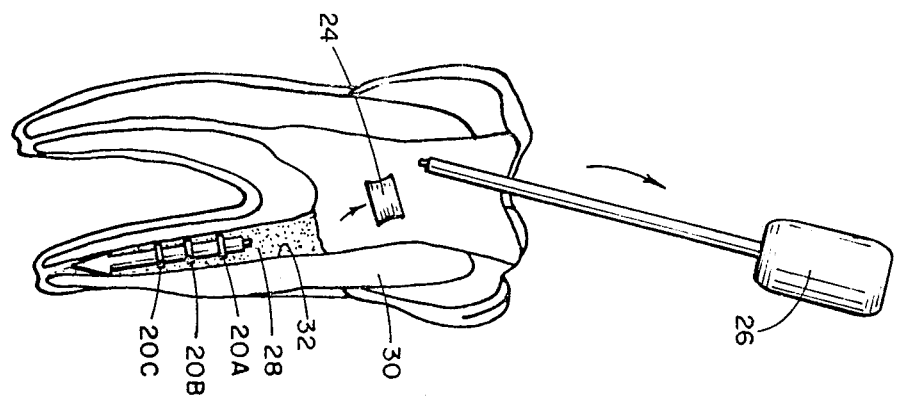
FIG. 6 shows the removal of the proximal portion of the appliance with the distal portion being retained in the root canal with the filler material.

FIGS. 4 through 6 show the continuation of the step of filling root canal 32. FIG. 4 shows the appliance inserted into the canal 32. The filler material 28 is forced by the insertion of the appliance to fill the canal to the apical area 36 of the tooth. After full insertion of the appliance as shown in FIG. 4, rotational torque is applied to handle 26 severing the shaft at the reduced torque resistance area 22 as shown in FIG. 5. This is possible since the flared distal end 18 of the shaft resists rotation relative to tooth 30.

After the shaft has been severed into two portions, the proximal portion is withdrawn. The sliding washer 24 is used to retain the filling material 28 in the canal by holding the washer downwardly as the proximal end portion of the shaft 12 is withdrawn.

FIG. 6 shows the proximal portion of the appliance being withdrawn. Washer 24 is then removed leaving the distal portion of the shaft in place within the root canal 32. The root canal 32 can be more completely filled by applying additional filler material and by applying mechanical or hydraulic pressure to the filler material to force it into the root canal. The coronal area of the tooth can be filled in the usual way.

The depiction of the tooth 30 in FIGS. 3 through 6 is merely exemplary as teeth are individualistic and the drawings are intended to exemplify the steps involved rather than to accurately pictorially represent the appearance of the tooth or root canal therein.

The appliance of this disclosure thus provides a unique and very effective way of conveying filler material, such as gutta-percha, into an endodontically prepared root canal. The prior art teaches the use of a file as a carrier of filler material, however, this known method, while functioning successfully for its intended purpose, nevertheless has limitations and problems which are overcome by the present invention.

FIG. 7 shows an alternate embodiment of the invention in which the appliance 10 includes a shaft in which the proximal portion 40 and distal portion 42 are integral with each other. The distal portion is tapered and includes a spiral groove 44. The groove 44 has generally flat outer edges; that is, the groove 44 is for the purpose of retaining the filler material on the distal portion. Further, the use of the spiral groove 44 has the advantage that after the distal portion with the filler material thereon is inserted in a root canal and the tool can be rotated slightly so as to additionally compact and condense the filler material.

When using the appliance of FIG. 7, the dentist, after inserting the appliance having filler material thereon into an endodontically prepared root canal, can, rather thana leave the distal portion in the root canal as previously discussed, completely remove the appliance. This technique is accomplished in the following manner. First, the appliance distal portion 42 having filler material thereon, such as shown in FIGS. 2 and 3, is inserted into the root canal. The dentist then rotates the appliance, by means of handle portion 26, in the counterclockwise direction while applying a slight force in the direction towards the tooth. The distal portion 42 can thus be backed completely out of the root canal, leaving the filler material therein. As the distal portion is advanced out of the root canal the auger action of spiral groove 44 compacts the filler material in the root canal.

In another technique the dentist can rotate the appliance counterclockwise ½ to a full turn, stop rotation and apply pressure on the appliance towards the tooth, rotate again ½ to a full turn, stop and apply pressure towards the tooth, sequentially repeating the steps until the distal portion 42 is completely removed from the root canal. This sequence of rotation followed by compaction utilizes the auger characteristic of the spiral groove 44 to achieve an effective filling of the root canal with filler material.

The spiral groove 44 in the distal portion 42 is formed to achieve an auger action and to refrain from causing a drilling action. That is, the flares are formed with symmetrical outer edges so as not to tend to cut into the tooth in which the appliance is placed and in which the tool is rotated for auger purposes.

Thus the embodiment of FIG. 7 can be used in the technique wherein the appliance distal portion is left in the root canal or in which the distal portion is completely removed. A further advantage of the embodiment of FIG. 7 is that the provision of spiral groove 44 makes the appliance distal portion more flexible so that it will more easily conform to the shape of a non-linear root canal.

It should be noted that in FIG. 7 the appliance does not include a severance point. The appliance of FIG. 7 is exemplary of the use of any of the appliances which are illustrated herein; which, instead of including a preselected severance point, are provided without a severance point. In the use of the appliance in FIG. 7 after the distal portion 42 has been inserted into a tooth, the dentist can sever the shaft such as by the use of a high speed burr or by cutting pliers. The severance can be used to merely form a point of weakness and thereafter the proximal portion separated from the distal portion by moving the proximal portion back and forward until it breaks or by the use of the high speed burr, cutting plier, or other means to completely sever the two portions. The shaft should be severed below the tooth coronal area 38 as seen in FIG. 5; that is, within the interior confines of the tooth so that when the root canal and any portion of the coronal area of the tooth which has been excavated is completely filled, the distal portion 42 remains completely retained within the tooth.

In the method of practicing the arrangement of FIG. 7 wherein no preselected point of separation between the distal and proximal portions are employed, the steps for filling an endodontically prepared root canal includes, first, filler material is formed onto the distal end portion of the elongated slender shaft formed of material having high biological tolerance. Next, the shaft having the filler material thereon is positioned within the root canal utilizing the handle portion secured to the shaft proximal portion. The final step is severing the shaft proximal portion from the distal portion leaving the distal portion and filler material carried thereby in the root canal The severance of the proximal from the distal portion can be carried out by operation of severance means carried by the shaft which severance means can be such as the circumferential groove or area of weakness 22, as described with reference to FIG. 1, or another means as hereinafter described. The step of severing the shat proximal portion from the distal portion includes the application of severance force to the shaft, such as by a high speed rotary burr or the use of cutting pliers, or some similar mechanical means.

FIG. 8 shows a still alternate embodiment of the invention which includes a severance point 22 which is optional as any of the embodiments can be utilized either with or without a severance means. The distal portion 42 includes integral burrs 46 extending from the surface to aid in supporting the filler material on the distal portion.

FIG. 9 shows the embodiment having the optioal severance point 22 and wherein the distal portion 42 is of non-circular cross-section configuration.

FIGS. 12A, 12B and 12C show examples of such noncircular cross-sectioal configuration. FIG. 12A shows the arrangement wherein the distal portion 42 is of triangular cross-section; FIG. 12B shows an oval crosssectional configuration; and FIG. 12C shows a square cross-sectional configuration. Such non-circular crosssectional configurations augment the retention of filler material onto the distal portion.

FIG. 10 shows another embodiment of the invention which includes a defined point of separation. In FIG. 10 the distal portion 42 has, at the upper end 42A thereof, a recess 48 therein. The shaft proximal portion 40 has a reduced external diameter extension portion 50 which is telescopically received within recess 48. In this manner the distal and proximal portions 42 and 40 are retained in axial alignment while the filler material 28 is being secured to the distal portion and while the distal portion with filler material thereon is inserted into the root canal. Thereafter, the proximal portion 40 is easily separable from the distal portion.

FIG. 11 shows a still different means of achieving separation. In this embodiment the distal upper end 42A is secured to the proximal end 40A by means of an adhesive 52. The adhesive is sufficient to retain the distal and proximal portions 42 and 40 in axial alignment while the filler material 28 is applied and while the distal portion with attached filler material is inserted into a root canal, but allow the portion to be separated by bending the proximal portion relative to the distal portion to break the adhesive 52.

Thus, FIGS. 7-11 show first a variety of means of improving the retention of the filler material aon the shaft distal portion. Second, they demonstrate two methods of practicing the invention, one, as in FIG. 7, wherein no preselected portion of separation is provided and the dentist performs separation after the distal portion is inserted into the root canal, whereas in FIGS. 8-11 various types of arrangements are provided for a preselected point of separation. The arrangement of FIG. 7 has the advantage that the tool can be designed wherein the primary consideration is the diameter rather than the depth of the root canal, whereas in the arrangements of FIGS. 8-11 the tool is preferably pre-designed both to accommodate the diameter of the root canal as well as the depth of the root canal. By //s// reference to accommodation of diameter root canal means that the appliance can be manufactured in a variety of diameters so that the dentist can select the maximum diameter which can be easily accommodated by the endodontically prepared root canal to thereby require a reduced amount of filler material whereas it can be seen; however, that only a limited number of diameters are required since there is no mandatory requirement that the diameter of the appliance distal portion closely match the diameter of the root canal.

While FIGS. 7, 8 and 9 show appliances 10 with filler material formed on the distal portion 42, it is understood that such appliances may normally be supplied to dentists with the filler material pre-formed on the distal portions as in FIGS. 10 and 11.

As previously mentioned herein, the filler material used for obdurating endodontically prepared root canals may be such as gutta-percha. Gutta-percha has been the most commonly used filler material for such purpose since its introduction over 100 years ago. Gutta-percha is obtained from the latex from sapotaceous trees and is a trans-isomer of polyisoprene and differs from natural rubber due to its crystalline structure.

Gutta-percha in its material state is in an "alpha" crystalline form, but when heated above 65° it becomes amorphous and melts. When it cools it returns to a "beta" crystalline state, unless cooled at a very slow rate. Thus, it is the "beta" crystalline form which is commonly used in endodontics. Further, commercially prepared gutta-percha material for endodontics is usually a mixture of gutta-percha beta crystalline form with a filler, such as zinc oxide, with other minor ingredients including heavy metal sulphates, waxes or resins to achieve the desired characteristics of the end product.

In addition, gutta-percha is sometimes mechanically treated to change its physical characteristic for use in endodontics. U.S. Pat. No. 4,632,977 teaches a method of plasticizing thermoplastic polymers, including gutta-percha, to change their physical characteristics.

The present invention contemplates the us of filler materials of any composition or formulation which has physical and biological tolerance properties adaptable for use in obdurating root canals. The term "filler material" as used herein includes gutta-percha in either the alpha or beta crystalline state, and including compositions including mixtures of other materials with gutta-percha, or any other filler material having similar properties for use in filling endodontically prepared root canals.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without department from the spirit and scope of this disclosure. It is understood that the invention is not limited to the embodiments set forther herein for purposes of exemplification, but is to be limited only by the scope of the attached claim or claims, including the full range of equivalency to which each element thereof is entitled.

What is claimed is:

1. An appliance for applying a filler material such as gutta-percha or the like to an endodontically prepared root canal of a tooth, comprising;

an elongated shaft having a distal portion and a proximal portion and of length such that the distal portion is positionable in at least substantially the full length of the root canal, at least the shaft distal portion being of material having high biological tolerance, and the distal portion having a spiral groove formed on the exterior surface thereof;

filler material formed onto said distal portion, the spiral groove serving to improve retention of the filler material and for augering the filler material into a root canal when the appliance is rotated after insertion into a root canal, said distal portion of said shaft being severable from said proximal portion, the distal portion remaining in the root canal and, in conjunction with said filler material, serving to fill the canal; and a manually manipulatable handle portion at said shaft proximal portion.

2. An appliance according to claim 1 wherein said shaft distal portion is secured to said shaft proximal portion by a telescopic fit forming said means of severing said shaft proximal portion from said shaft distal portion.

3. An appliance according to claim 1 wherein said shaft distal portion is secured to said shaft proximal portion by a bonding adhesive forming said means of severing said shaft's proximal portion from said shaft distal portion.

4. An appliance according to claim 1 wherein said shaft includes a reduced cross-sectional area portion intermediate said shaft distal and proximal portions forming said means of severing said proximal portio of said shaft from said distal portion.

5. An appliance according to claim 1 wherein said proximal portion is severable from said distal portion by application of severing force after said distal portion has been inserted into a root canal.

6. An appliance for applying filler material, such as gutta-percha or the like, to an endodontically prepared root canal of a tooth, comprising:

a shaft distal portion of material having high biological tolerance and of length to extend at least substantially the full depth of a tooth root canal and having an external surface adaptable to receive filler material thereon, the distal portion having a first end and a second end;

a shaft proximal portion forming a handle portion and having a first end and a second end, the shaft distal portion second end having a recess therein, and the shaft proximal portion first end having a reduced cross-sectional area integral portion which is telescopically removably receivable in said distal portion recess; and filler material formed onto said shaft distal portion.

7. An appliance according to claim 6 wherein said shaft proximal and distal portions are in substantial alignment when said reduced cross-sectional area portion is fully received in said recess.

8. An appliance according to claim 6 wherein said shaft proximal portion first end has a recess therein and said shaft distal portion first end has a reduced diameter end portion removably telescopically receivable in said proximal portion recess.

9. An appliance according to claim 8 wherein said shaft proximal and distal portions are in substantial alignment when said reduced cross-sectional area portion is fully received in said recess.

10. An appliance according to claim 6 wherein said shaft distal portion is triangular in cross-section.

11. An appliance according to claim 6 wherein said shaft distal portion is oval in cross-section.

12. An appliance according to claim 6 wherein said shaft distal portion is square in cross-section.

13. An appliance according to claim 6 wherein said shaft distal portion was a spiral groove in the exterior surface thereof.

14. An appliance according to claim 6 wherein said shaft distal portion has integral projections extending from the external surface.

15. An appliance for use in applying filler material, such as gutta-percha or the like, to an endodontically prepared root canal of a tooth, comprising:

a shaft first, distal portion of material having high biological tolerance and of length to extend at least substantially the full depth of a tooth root canal and having an external surface adaptable to receive filler material thereon and having a first end and a second end;

a shaft proximal portion forming a handle portion and having a first end and a second end, the shaft distal portion second end and said shaft proximal portion first end being configured for mating engagement with each other;

a severable bonding material between said shaft portion's mating surfaces; and filler material formed onto said shaft distal portion.

16. An appliance according to claim 15 wherein said shaft proximal and distal portions are in substantial alignment when said distal portion second end is secured by said bonding material to the said proximal portion first end.

* * * * *

UNITED STATES PATENT AND TRADEMARK OFFICE
CERTIFICATE OF CORRECTION

PATENT NO.   : 4,894,011

DATED        : Jan. 16, 1990

INVENTOR(S)  : Johnson

It is certified that error appears in the above-identified patent and that said Letters Patent is hereby corrected as shown below:

Column 2, line 55, change "guttapercha" to --gutta-percha--.
Column 5, line 16, change "thana" to --than--.
Column 6, line 35, change "optioal" to --optional--; line 39, change "cross-sectioal" to --cross-sectional--.
Column 7, line 2, change "aon" to --on--; line 15, delete "//s//"; line 55, change "us" to --use--.
Column 8, line 51, change "portio" to --portion--.

Signed and Sealed this

Fifth Day of May, 1992

Attest:

DOUGLAS B. COMER

*Attesting Officer*               *Acting Commissioner of Patents and Trademarks*